United States Patent [19]
Stenstrom

[11] 3,964,295
[45] June 22, 1976

[54] METHOD AND DEVICE FOR ASCERTAINING SMALL AMOUNTS OF OIL IN WATER
[75] Inventor: Börje Harald Stenstrom, Enebyberg, Sweden
[73] Assignee: Salen & Wicander AB, Sundbyberg, Sweden
[22] Filed: Aug. 6, 1974
[21] Appl. No.: 495,179

Related U.S. Application Data
[63] Continuation-in-part of Ser. No. 340,152, March 12, 1973, abandoned.

[52] U.S. Cl. .............................. 73/61.1 R; 356/70
[51] Int. Cl.² ........................................ G01N 21/06
[58] Field of Search ............ 73/61.1 R, 61 R, 61.3, 73/53, 19, 17 A, 15.4; 356/36, 70, 85, 201

[56] References Cited
UNITED STATES PATENTS

| | | | |
|---|---|---|---|
| 2,897,671 | 8/1959 | Phelan et al. | 73/53 |
| 3,133,437 | 5/1964 | Remke et al. | 73/61.1 R |
| 3,253,606 | 5/1966 | Kuntz | 73/61.1 R X |
| 3,612,887 | 10/1971 | Canevari | 356/70 |
| 3,627,419 | 12/1971 | Thevenier | 356/36 |
| 3,824,016 | 7/1974 | Woodriff et al. | 356/85 |

Primary Examiner—Richard C. Queisser
Assistant Examiner—Joseph W. Roskos
Attorney, Agent, or Firm—Fred Philpitt

[57] ABSTRACT

For determining or indicating the oil content of small amounts of oil in water a defined amount of water is removed so that the oil is concentrated in the water, and thereafter the oil content in the concentrated oil-water mixture is measured. So as to concentrate the oil, the oily water can pass a filter material, the color change or dielectric constant of which is measured. As an alternative, the oily water is concentrated in a rotating cyclone or centrifuge so that substantially all oil is accumulated in the center together with a smaller portion of the original water volume. The clarity of the water is then determined and considered as a measure of the oil content.

8 Claims, 8 Drawing Figures

METHOD AND DEVICE FOR ASCERTAINING SMALL AMOUNTS OF OIL IN WATER

RELATED APPLICATION

This application is a continuation-in-part of prior application Ser. No. 340,152, filed Mar. 12, 1973, and now abandoned.

BACKGROUND

There are a number of different devices which have been proposed for indicating the presence of oil in water. However, they do not permit an exact determination of the oil content and, further, they suffer from such disadvantages as complicated design, need of calibration for salt contents in the water, different water temperatures, etc. A special problem of indicating the amount of oil in water is that the type of oil and the quality of the oil that is in the water may vary quite considerably. For instance there are many, many different types of crude oils and many, many different types of refined hydrocarbons that are shipped in tankers and which may be present in a refinery. Accordingly, any instrument that is intended for monitoring oil in water should desirably be independent of the quality of the oil. Only then can the recorded oil content serve as evidence proving whether discharged amounts of oil have been within permitted limits or not.

OBJECTS

An object of the present invention is, while eliminating these disadvantages in previously known devices, to achieve a simple, rugged and reliable method and a device for determining the content of oil in water as low as one part per 100,000.

THE PRESENT INVENTION

The present invention relates to a method and a device for determining the oil content of small amounts of oil in water. The invention is intended to be utilized on board ships, in industries, etc., where large amounts of water are pumped out and where surveillance of the possible presence of oil is necessary and frequently regulated by legislation.

The method according to the present invention is generally characterized by the removal of a defined amount of water so as to concentrate or enrich the oil in the water and measuring the oil content in the concentrated oil-water mixture.

THE INVENTION MORE SPECIFICALLY

In a preferred method of applying the invention, the oil is concentrated by making a predetermined amount of oily water per unit of time pass a determined area of a filter material which absorbs or separates oil. The oil content can thereafter be measured photo-electrically by determination of the color change of the oil-absorbing filter material. According to an alternative application of the invention the oil content is determined by measurement of the dielectric constant of the oil-absorbing filter material.

If the filter material according to one embodiment of the invention is impregnated prior to passage of the oily water with an oil-soluble (but not water-soluble) color substance, determination is also possible of any presence of refined oils with little color substance of their own.

In a preferred method of applying the invention the oily water is conducted in a back and forth direction through the filter material. The greater part of rust and solid particles will by this means be led away, while existing oil is retained.

As filter material it is suitable to utilize a thin strip of polypropylene wool.

According to one modification of the invention the oily water is concentrated in a rotating cyclone or centrifuge, whereupon essentially all oil is concentrated in the center together with a predetermined or measureable smaller portion of the original water volume. The oil content is thereafter determined by photo-electrical means through registration of the clarity of the water.

The invention also relates to a device for indication of small amounts of oil in water during application of the above described method.

THE DRAWINGS IN GENERAL

Several embodiments of the invention will now be described in greater detail with reference to the accompanying drawings wherein.

SPECIFIC DESCRIPTION OF THE DRAWINGS

Figure 1:
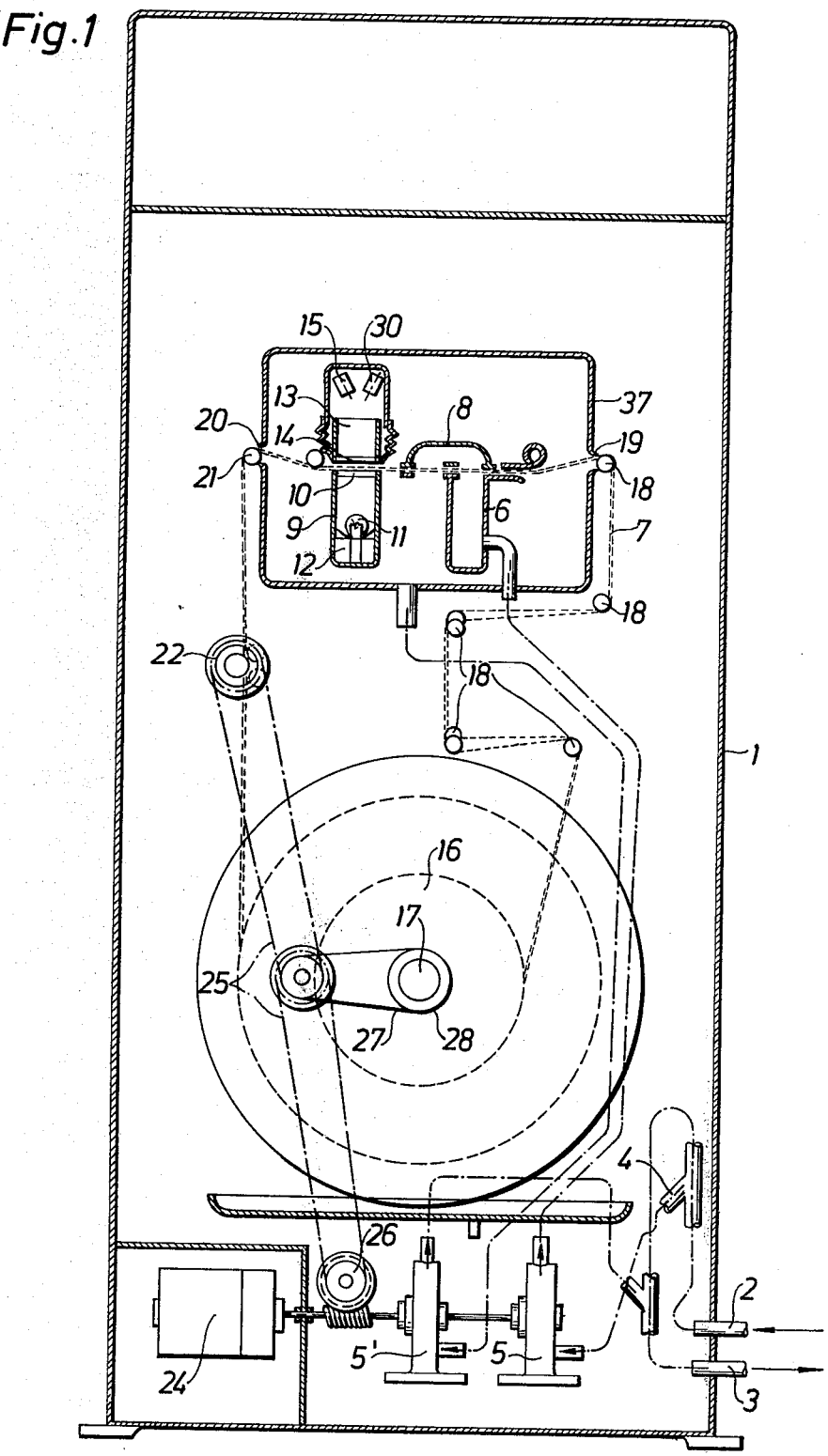
FIG. 1 shows the interior of a casing containing the essential parts of a device according to the present invention which are intended for a ship.

The device or apparatus shown in FIG. 1 for determining the oil content of small amounts of oil in water, intended in the first instance for ships, is enclosed in a casing 1 provided with a conduit 2 for incoming test water and a conduit 3 for outgoing test water. Since the test water taken from a ships line must amount in terms of volumetric flow to a certain minimum value in order to correspond to suitable pipe sizes, transport time for the test water through the piping system, etc., the major part of the water continues directly to the outlet 3. A small amount of test water is taken out through the connection 4, which is so designed that solid particles, on account of their dynamic force, have a tendency to accompany the main stream and are not included in the final test water. The test water is pumped by a pump 5 preferably a constant displacement rotor pump, and is conducted to a test chamber 37.

In the test chamber 37 the water sample enters from below and is conducted at a constant relatively low velocity through a chamber 6 (which has a square section) and then up through a filter band 7. The water then enters a housing 8 and undergoes a 180° change in the direction of flow and passes again from above down through the filter band 7. The water then flows freely out into the test chamber 37 and is carried away by the return pump 5' and conduit 3.

The filter band 7 consists essentially of tightly spun polypropylene wool and has such properties that oil is rapidly and completely absorbed by it, although its permeability to water is high. Solid particles such as rust, soil, sand, etc., adhere to the surface of the filter band during the first passage (i.e. to the bottom side of the band) but are flushed off again when the water reverses flow in chamber 8 and flows down through the band. The oil will remain in the band, however.

Immediately after serving its filtering function the filter band passes a photo-electrical device which consists of a lower sleeve 9, which at the top is terminated by a glass disc 10 and at the bottom is equipped with a light bulb 11 in a suitable holder 12. Arranged above the band in a similar manner is a sleeve 13 with a glass disc 14. Inside the sleeve 13 is a photo-electric cell 15. The upper sleeve 13 is movable and rests by spring action against the filter band 7.

The filter band is wound onto a coil or drum 16, which is freely mounted on a shaft 17. The filter band is led over guide rollers 18 and through a seal 19 into the test chamber 37. After the photo-electric cell the band is passed through a seal 20, over a roller 21, between three motor-driven rollers 22 to the coil or drum 23. The motor-driven rollers 22 are driven from an electric motor 24 via a chain drive 25 and a worm gear 26, so that the band is given a suitable low, constant speed. The coil or drum 23, onto which the used band is wound, is driven by a belt 27, which is free to slip over a driving disc 28, so that the band is continuously wound up despite a varying rotational speed being required as a result of the diametric change of the coil.

Figure 3:
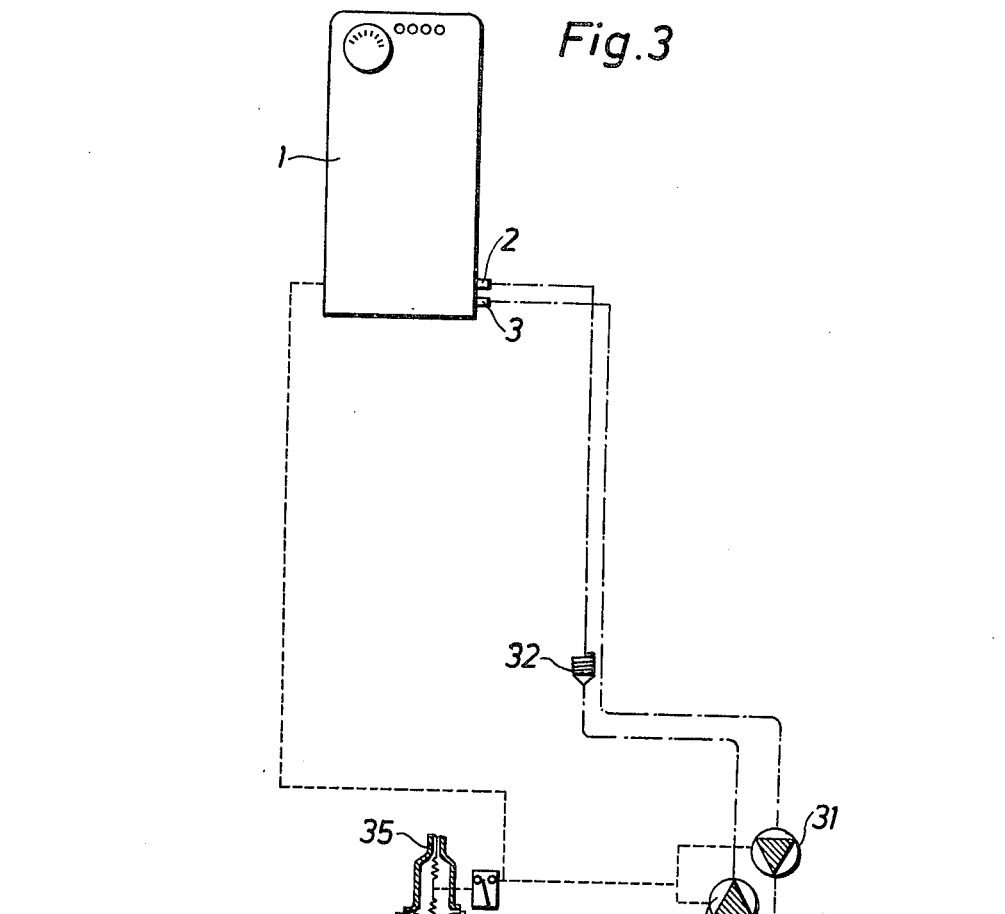
FIG. 3 is a sketch, illustrating an outlet line which is to be kept under surveillance and the principal parts of the required measuring equipment.

According to FIG. 3 continuous sampling is carried out from a line 45, the outlet of which has to be kept under surveillance. For this a pitot tube 29 is used according to known techniques. A selected water sample is pumped by a pump 30, (preferably a rotary pump) in a pipe coil connected to the test apparatus. A certain amount of surplus water must be pumped in order for a suitable water velocity to be obtained in a line with dimensions suitable for ships installation. The surplus water is recirculated and fed by another pump 31 back into the monitored line 45. By this means it is ensured that the flow in the test line will be essentially independent of the hydrostatic pressure in the monitored line, i.e. the draft of the ship. The water sample from the test chamber is also conducted back to the return line. Since the return pump 31 has a greater capacity than the pressure pump 30, the return of the test water can be continuously assured. Spring-loaded pressure-maintaining valves 32 and 33 serve to keep the line closed when the apparatus is not at work and to balance in a suitable way the pressures in the pipe coil.

In order to ensure that the apparatus is in operation when the pumping out of water takes place, there is preferably provided a further pitot tube 34, which actuates a pressure switch 35 of known design. This pressure switch starts all functions in the monitoring system when a predetermined flow rate in the monitored line is sensed. When the flow ceases the apparatus stops.

For indication of the remaining amount of filter strip in the apparatus use can be made of yet another photoelectric cell that is separately coupled to an amplification and indication circuit, which reacts to the light intensity that occurs in the event that no band passes between the photo-electric cell and the light source. A perforation in the band gives a signal when band remains for a certain time, for example an hour, and a suitable signal lamp then remains lighted.

The electrical equipment that senses the photo-electric cell 15 is based on known technique and consists of a suitable amplifier, a scale graduated in millionths of oil content and a warning indication when a designated value is exceeded. An out-signal can be connected to a continuous recorder and/or operatively connected to pumps, valves, etc, to prevent continued pumping out of water with too high an oil content.

As noted previously, the filter band consists essentially of a thin, homogeneous mat of polypropylene wool, which has the property of absorbing oil but gives good permeability of water. The filter band can also be impregnated with an oil-soluble, but not water-soluble, color substance, whereby refined oil products (which in themselves have a color content less than the heavier hydrocarbons such as crude oil) cause a corresponding indication by precipitation of the band's color substance.

Measurement of the oil content in the filter band can also take place by determining the change of the dielectric constant in the band as a function of its oil content. Instead of a light source and photo-electric cell, a condenser plate is arranged on either side of the band, the said plates being electrically insulated from each other. A high-frequency alternating voltage is applied to one plate and the out-signal obtained from the other plate, after suitable signal treatment according to known techniques, gives a measure of the oil content. Indication equipment, etc., are thereafter essentially in accordance with that described heretofore.

Figure 4:
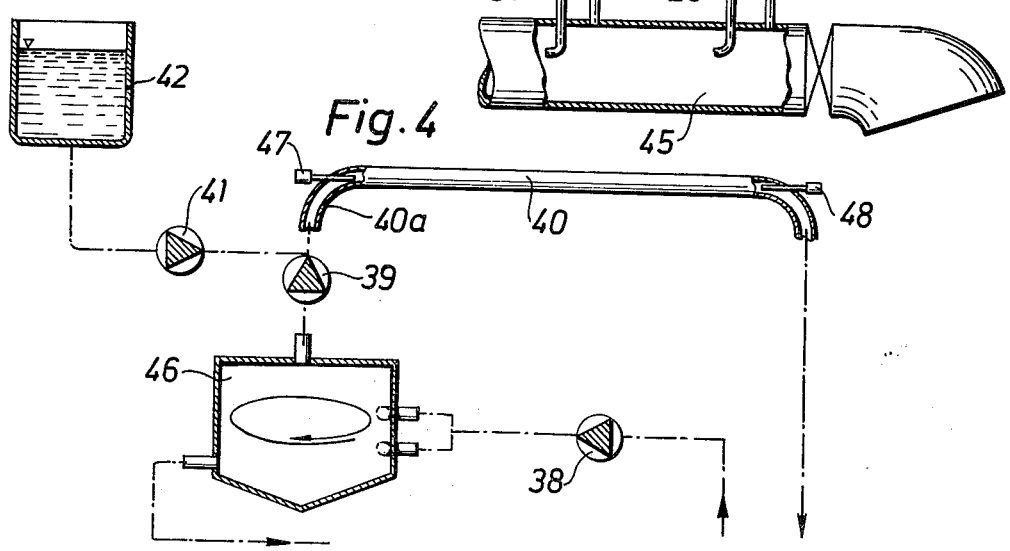
FIG. 4 illustrates a modified method of applying the invention.

FIG. 4 illustrates a modified method of concentrating the oil content in some test water. The test sample, which is pressurized by a pump 38, is conducted to a cyclone 46, in which the oil, as a consequence of its rotation in the cyclone, has a tendency to accumulate towards the center of the cyclone. A known volumetric flow is pumped out with pump 39 from the central part of the cyclone unit and will then essentially contain most of the oil in a suitably tenfold reduced amount of water. The surplus water is led from the cyclone on to the return line of the system. The thus concentrated oil-water mixture is sufficient to be visually observable. It is led to a horizontal pipe 40 limited by two 90° pipe bends 40a, in one of which is mounted a light source and in the other of which is mounted a photo-electric cell. In order to homogenize the oil droplets in the water and to prevent them from adhering to either the light source or the photo-electric cell, a dispersing agent is added continuously via a pump 41, which is connected to a container 42. The dispersing agent also contains a color substance, which is oil-soluble but not water-soluble, whereby a corresponding color indication or color emphasis is also obtained from refined oil products in a manner similar to that described heretofore.

According to another preferred embodiment of my invention I employ a combination of a discoloration measurement (indicated as reduced light reflection from the oil absorbant filter band) and a measurement of the gas evaporated when the filter band and hence the oil sample is heated to a pre-determined temperature. Since a heavy oil is usually dark in color and normally contains a higher percentage of heavy non-volatile components and a light oil normally has less color but contains a higher amount of volatile components, a combination of the two measurements just mentioned will give a better indication of oil content over a wide range of conditions than if only one type of measurement was used.

Figure 5:
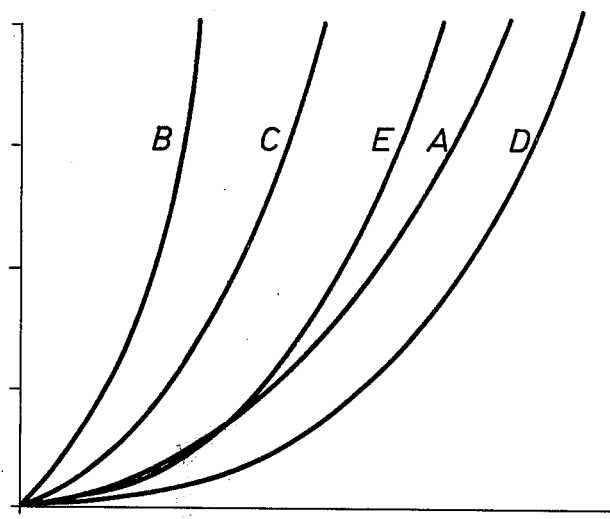
FIGS. 5, 6 and 7 are oil analysis curves.
Figure 6:
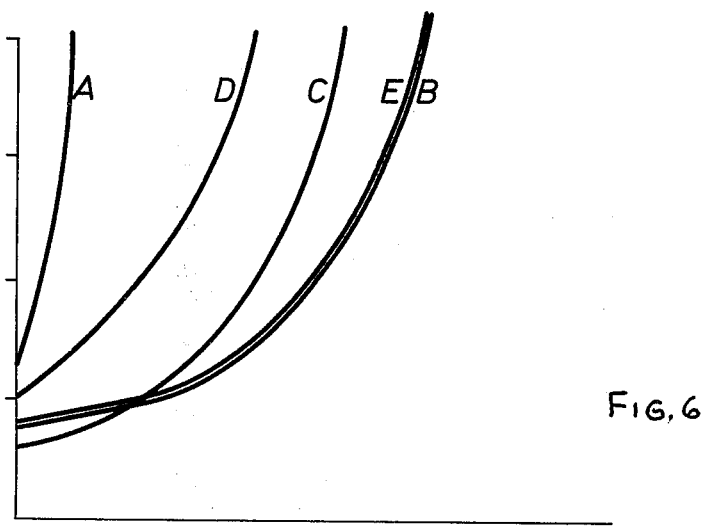
Figure 7:
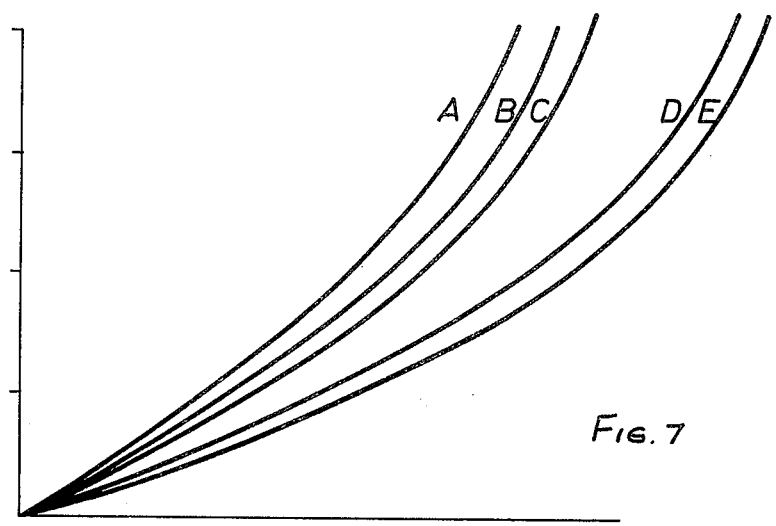

FIGS. 5 and 6 illustrates different curves derived from development work. FIG. 5 indicates the response curve from light reflection along. FIG. 6 the response curves based on gas evaporation alone. FIG. 7 indicates the response surves for the same oils, based on combined signals of light reflection and gas evaporation. The result in FIG. 7 represents typically the spread achieved when a large number of various crude oils and refined petroleum products are added together and represents an overall measuring accuracy of about ±25 percent, which is comparable to that achieved by laboratory type batch analyzing equipment.

Figure 2:
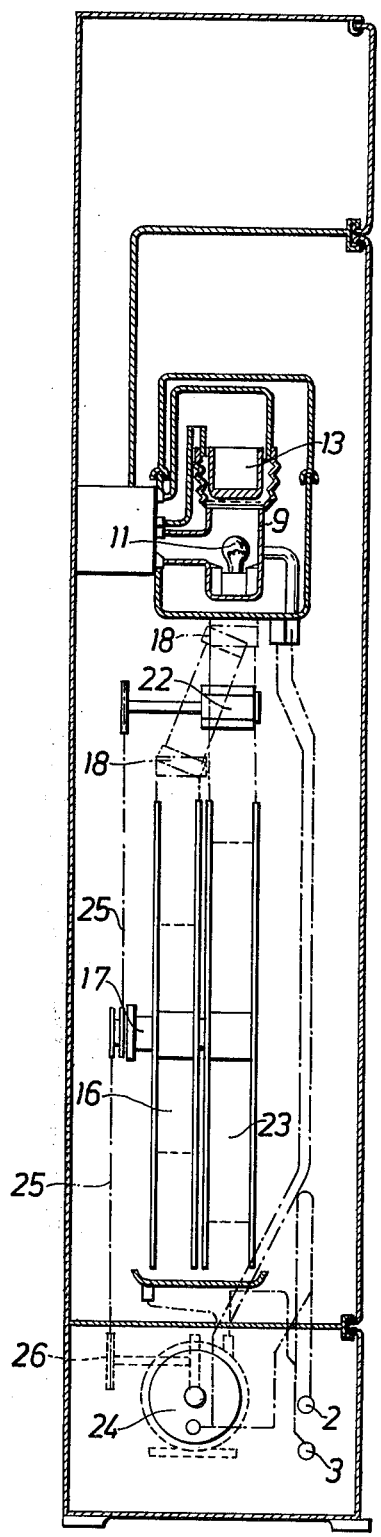
FIG. 2 shows the interior of a casing according to FIG. 1 viewed from the side.
Figure 8:
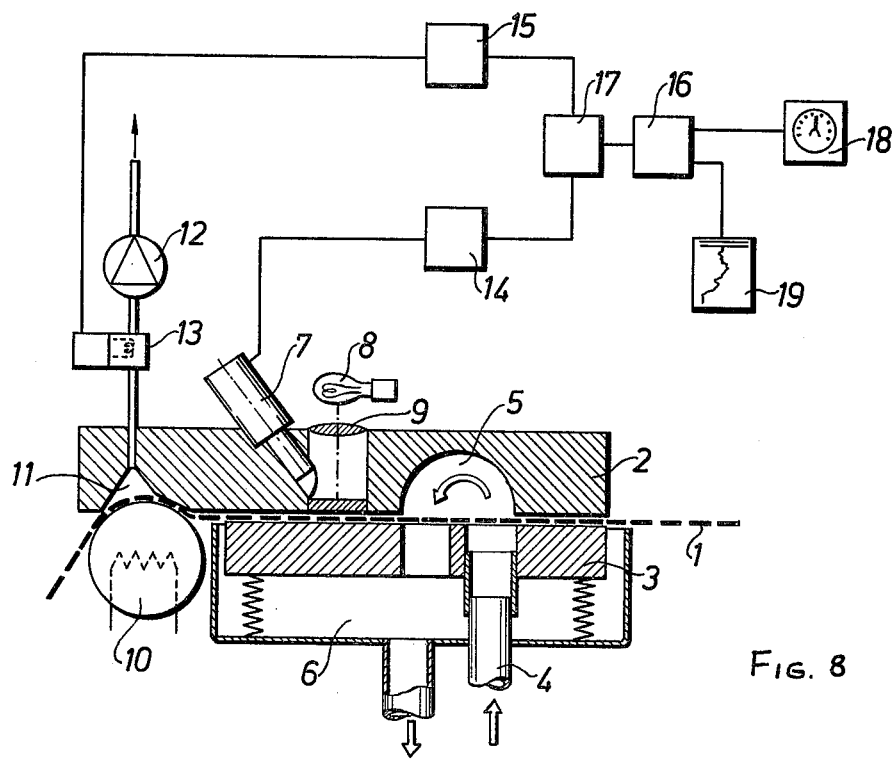
FIG. 8 illustrates another embodiment of the present invention.

FIG. 8 shows the measuring chamber only, the surrounding auxilliary arrangements for feeding the sample water and the filter band being identical to those described in FIGS. 1 and 2.

In FIG. 8, the filter band 1 is passed between the fixed body 2 and the spring loaded body 3 providing suitable clamping around the filter band. Sample water is supplied through a pipe 4, forced through the filter band, turned around in cavity 5 and collected in the bottom of the test chamber 6 for further removal by a scavenge pump (not shown).

An important feature of this arrangement is that all kinds of solids in the water are filtered out on the underside of the filter band and only oil penetrates the filter band and creates a discoloration on the top surface of the band. The discoloration of the band is monitored by a photocell 7 working together with a light source 8 and a condensor lens 9. The filter band is further routed over a drum 10 kept at a constant preselected temperature (50°– 70°C, preferably 60°C). A cavity 11 is arranged above the heating drum, having only a small slot opening along its periphery. A gas pump 12 of a known design draws a steady flow of air through the slots, through the cavity and past a gas detector 13 of known type to the pump and further expelled to the open air. The hydrocarbon gas concentration in the steady flow of atmosphere is related to the amount of hydrocarbon gas evaporated from the filter band as it passes over the heating drum 10.

The signals from the photocell and from the gas detector are amplified individually in amplifiers 14 and 15 of any known design and added to the final amplifier 16 after having passed a signal dividing arrangement 17 whereby the mixing ratio of the two signals may be controlled. The output signal from amplifier 16 is further presented on an instrument 18 and a recorder 19 of any known design.

What I claim is:

1. A method for continuously determining the oil content of a water stream containing small amounts of oil, comprising the steps of:
   a. continuously removing a representative sample of said water stream,
   b. continuously passing said representative sample of said water stream through a moving mass of filter material which is capable of removing at least a portion of the oil contained in said representative sample,
   c. subjecting said moving mass of filter material containing removed oil to photo-electric analysis to thereby obtain an indication of the color changes in the filter material, and
   d. passing said filter material through a zone where hydrocarbon gases can evaporate from said filtering material,
   e. obtaining an indication of the amount of hydrocarbon gases evaporated in said zone by gas detecting means, and
   f. correlating the oil color change indication obtained by photo-electric analysis with the indication of the amount of hydrocarbon gases to arrive at an indication of the oil content of the water.

2. A method according to claim 1 wherein the hydrocarbon gas evaporation is achieved by passing the mass of filter material over a heated body with a temperature of 50°–70°C.

3. A method according to claim 1 wherein the representative sample is passed through the mass of filter material twice, with opposite direction of flow, whereby the greater part of rust and other solid particles will be flushed away from the mass of filter material.

4. A method according to claim 1 wherein the flow rate of the water stream containing oil is maintained under surveillance and the flow thereof operatively connected to the activation of the photoelectric analysis and the measurement of evaporated hydrocarbon gases.

5. An apparatus for continuously determing the oil content of a water stream containing small amounts of oil, which comprises:
   a. a conduit for removing a representative sample of said water stream and conducting it to a filtering zone,
   b. a filtering zone containing a band of filtering material,
   c. a conduit for conducting said representative sample to said filtering zone,
   d. means for passing said band of filtering material through said filtering zone,
   e. conduit means for removing water from said filtration zone after it has passed through said filtering material,
   f. a first zone containing a photoelectric analyser of the color of said filtering material,
   g. a second zone containing a detector for evaporated hydrocarbon gases,
   h. means for passing said filtering material through said first and second zones, and
   i. means for correlating said photoelectric analyzer output with the gas detector to arrive at an indication of the oil content of the water.

6. A device according to claim 5 including means for heating the filtering material to promote gas evaporation.

7. A device according to claim 5 including a pump with constant displacement for introducing the oil and water, the filtering material band being wound onto a first supply roll and arranged to be wound up after passing through the photoelectric analyser and the gas detector onto a second roll.

8. A device according to claim 5 including means for advancing the filtering material with constant speed past said photoelectric analyzer and the gas detector.

* * * * *